United States Patent
Underwood et al.

(10) Patent No.: US 8,428,963 B2
(45) Date of Patent: *Apr. 23, 2013

(54) SYSTEM AND METHOD FOR ADMINISTERING HEALTH CARE COST REDUCTION

(75) Inventors: Howard R. Underwood, Bryn Mawr, PA (US); Walter Kastenschmidt, North Wales, PA (US)

(73) Assignee: Aetna Inc., Hartford, CT (US)

( * ) Notice: Subject to any disclaimer, the term of this patent is extended or adjusted under 35 U.S.C. 154(b) by 169 days.

This patent is subject to a terminal disclaimer.

(21) Appl. No.: 12/724,185

(22) Filed: Mar. 15, 2010

(65) Prior Publication Data

US 2010/0169124 A1    Jul. 1, 2010

Related U.S. Application Data

(63) Continuation of application No. 10/813,968, filed on Mar. 31, 2004, now Pat. No. 7,693,728.

(51) Int. Cl.
  *G06Q 50/00* (2012.01)
  *A61B 5/00* (2006.01)

(52) U.S. Cl.
  USPC ........................................ 705/2; 705/3; 705/4

(58) Field of Classification Search .................. None
  See application file for complete search history.

(56) References Cited

U.S. PATENT DOCUMENTS

| | | | |
|---|---|---|---|
| 5,486,999 A | 1/1996 | Mebane | |
| 5,692,501 A | 12/1997 | Minturn | |
| 5,835,897 A | 11/1998 | Dang | |
| 6,370,511 B1 | 4/2002 | Dang | |
| 6,385,589 B1 * | 5/2002 | Trusheim et al. | 705/2 |
| 7,392,201 B1 * | 6/2008 | Binns et al. | 705/4 |
| 2002/0128866 A1 * | 9/2002 | Goetzke et al. | 705/2 |
| 2005/0080462 A1 * | 4/2005 | Jenkins et al. | 607/58 |
| 2005/0222867 A1 | 10/2005 | Underwood et al. | |
| 2006/0178915 A1 | 8/2006 | Chao | |

OTHER PUBLICATIONS

"Health New England Chooses Symmetry Software: Provider to Asses Future risks with Episode Risk Groups™" Symmetry, an Ingenix Company, www.symmetry-health.com/PressReleases/PR_HealthNE.htm (Sep. 28, 2001). (1 page).

(Continued)

*Primary Examiner* — Robert Morgan
*Assistant Examiner* — Kristine Rapillo
(74) *Attorney, Agent, or Firm* — Leydig, Voit & Mayer LLC.

(57) ABSTRACT

A system and method for the efficient administration of health care plans, particularly as to the reduction and/or elimination of avoidable medical costs for select individuals who participate in the plan, is disclosed. Existing health care data is processed to determine an indication as to the relative desirability of an intervention in a plan participant's health care regimen. The data is also processed to determine the status of one or more flags, each of which potentially indicates the relative desirability of an intervention in a plan participant's health care regimen. A predictive model is used to determine the status of a flag relating to the likelihood of an insurance plan participant making a disability claim within a certain period of time. The information relating to desirability of an intervention in a plan participant's health care regimen, as well as a plan participant's medical information and claim history, is presented to case managers and/or health care providers in a user-friendly format.

18 Claims, 13 Drawing Sheets

OTHER PUBLICATIONS

"A New Approach to Health Risk Assessment," Symmetry, an Ingenix Company, www.symmetry-health.com/resource/ (May 2006) (16 pages).

"A Pharmacy-Based Approach to Health Risk Assessment", Symmetry, an Ingenix Company, www.symmetry-health.com/resource, (Jul. 2006) (12 pages).

"An Overview of Symmetry Pharmacy Risk Groups™ (PRGs)" Symmetry, an Ingenix Company, product listing, www.symmetry-health.com/prudocuts/product_SPRG.php (Page downloaded Oct. 12, 2006—no specific date, but not later than applicants filing date) (2 pages).

"An Overview of Symmetry Episode Risk Groups® (ERGs®)" Symmetry, an Ingenix Company, product listing, www.symmetry-health.com/prudocuts/product_SERG.php (Page downloaded Oct. 12, 2006—no specific date, but not later than applicants filing date) (3 pages).

Symmetry, an Ingenix Company, home page, www.symmetry-health.com/ (page downloaded Oct. 12, 2006—no specific date, but not later than applicants filing date) (1 page).

Symmetry, an Ingenix Company, patent listing, www.symmetry-health.com/products/patent.php (page downloaded Oct. 12, 2006—no specific date, but not later than applicants filing date) (1 page).

Symmetry, an Ingenix Company, product listing, www.symmetry-health.com/products/ (page downloaded Oct. 12, 2006—no specific date, but not later than applicants filing date) (2 page).

U.S. Appl. No. 10/813,968 Office Action dated Nov. 9, 2007.

Reply to Office Action dated Nov. 9, 2007 for U.S. Appl. No. 10/813,968.

U.S. Appl. No. 10/813,968 Office Action dated Jul. 25, 2008.

Reply to Office Action dated Jul. 25, 2008 for U.S. Appl. No. 10/813,968.

U.S. Appl. No. 10/813,968 Final Office Action dated May 26, 2009.

Reply to Final Office Action dated May 26, 2009 for U.S. Appl. No. 10/813,968.

U.S. Appl. No. 11/625,660 Office Action dated Dec. 28, 2009.

Reply to Office Action dated Dec. 28, 2009 for U.S. Appl. No. 11/625,660.

* cited by examiner

FIG. 8

| Date of Claim | Place of Service | Provider | Specialty of Provider | Primary Diagnosis | Procedure | Allowed Amount of Claim | Copay | Paid |
|---|---|---|---|---|---|---|---|---|
| 06/26/2003 | O | Dr. Daily | Cardiology | Coronary Atherosclerosis Of Na | Established Patient Office 3 | $X,XXX | $20 | Y |
| 06/26/2003 | O | Dr. Daily | Cardiology | Coronary Atherosclerosis Of Na | Electrocardiogram, Complete | $X,XXX | $0 | Y |
| 06/17/2003 | O | Dr. Daily | Internal Medicine | Long-Term (current) Use Of Ant | Established Patient Office 1 | $X,XXX | $15 | Y |
| 06/12/2003 | O | Dr. Daily | Internal Medicine | Long-Term (current) Use Of Ant | Prothrombin Time | $X,XXX | $0 | Y |
| 06/12/2003 | O | Dr. Daily | Internal Medicine | Long-Term (current) Use Of Ant | Established Patient Office 1 | $X,XXX | $15 | Y |
| 06/10/2003 | O | Dr. Daily | Internal Medicine | Long-Term (current) Use Of Ant | Prothrombin Time | $X,XXX | $0 | Y |
| 06/10/2003 | O | Dr. Daily | Internal Medicine | Long-Term (current) Use Of Ant | Established Patient Offi 2 | $X,XXX | $15 | Y |
| 06/06/2003 | O | Dr. Daily | Pharmacy Drugs | Other Unknown And Unspecified | Not Available/Applicable | $X,XXX | $0 | N |
| 06/06/2003 | O | Dr. Daily | Internal Medicine | Long-Term (current) Use Of Ant | Established Patient Offi 2 | $X,XXX | $15 | Y |
| 06/06/2003 | O | Dr. Daily | Internal Medicine | Long-Term (current) Use Of Ant | Prothrombin Time | $X,XXX | $0 | Y |
| 06/04/2003 | I | Dr. Daily | Cardiology | Intermediate Coronary Syndrome | Left Heart Catheterization | $X,XXX | $0 | Y |
| 06/04/2003 | I | Dr. Daily | Cardiology | Intermediate Coronary Syndrome | Intravas Us, Heart Add-On | $X,XXX | $0 | Y |
| 06/04/2003 | I | Dr. Daily | Cardiology | Intermediate Coronary Syndrome | Imaging Supervision Interp & | $X,XXX | $0 | Y |
| 06/04/2003 | I | Dr. Daily | Cardiology | Intermediate Coronary Syndrome | Injection For Coronary Xrays | $X,XXX | $0 | Y |
| 06/04/2003 | I | Dr. Daily | Cardiology | Intermediate Coronary Syndrome | Imaging Supervision, Interp | $X,XXX | $0 | Y |
| 06/04/2003 | I | Dr. Daily | Cardiology | Other Chest Pain | Injection For Heart X-Rays | $X,XXX | $0 | Y |
| 06/04/2003 | I | Dr. Daily | Cardiology | Other Chest Pain | Electrocardiogram Report | $X,XXX | $0 | Y |
| 06/02/2003 | I | Dr. Daily | Hospitals | Coronary Atherosclerosis Of Na | Not Available/Applicable | $X,XXX | $250 | Y |
| 06/02/2003 | I | Dr. Daily | Internal Medicine | Unspecified Chest Pain | Subsequent Visit 4 | $X,XXX | $0 | Y |
| 06/02/2003 | I | Dr. Daily | Cardiology | Other Chest Pain | Electrocardiogram Report | $X,XXX | $0 | Y |
| 06/01/2003 | I | Dr. Daily | Internal Medicine | Other Chest Pain | Subsequent Visit 3 | $X,XXX | $0 | Y |
| 05/31/2003 | I | Dr. Daily | Infectious Disease | Cardiovascular Disease, Unspec | Subsequent Visit 4 | $X,XXX | $0 | N |
| 05/31/2003 | I | Dr. Daily | Cardiology | Intermediate Coronary Syndrome | Subsequent Visit 3 | $X,XXX | $0 | N |

FIG. 9

| Date of Sales | Prescribing Provider | NDC Product Name | Drug Class | Days supply | Rx Paid Amount of Claim | Copay |
|---|---|---|---|---|---|---|
| 06/23/2003 | Dr. MacArthur | Warfarin Sodium | Coumarin Anticoagulants | 30 | $X,XXX | $30 |
| 06/13/2003 | Dr. MacArthur | Losartan Potassium | Angiotensin II Receptor Antago | 30 | $X,XXX | $15 |
| 06/06/2003 | Dr. MacArthur | Omeprazole | Proton Pump Inhibitors | 30 | $X,XXX | $10 |
| 05/13/2003 | Dr. MacArthur | Warfarin Sodium | Coumarin Anticoagulants | 30 | $X,XXX | $30 |
| 05/10/2003 | Dr. MacArthur | Levothyroxine Sodium | Thyroid Hormones | 90 | $X,XXX | $30 |
| 04/28/2003 | Dr. MacArthur | Omeprazole | Proton Pump Inhibitors | 30 | $X,XXX | $10 |
| 04/27/2003 | Dr. MacArthur | Warfarin Sodium | Coumarin Anticoagulants | 20 | $X,XXX | $15 |
| 04/26/2003 | Dr. MacArthur | Clarithromycin | Clarithromycin | 10 | $X,XXX | $10 |
| 04/26/2003 | Dr. MacArthur | Acetaminophen w/ Hydrocodone | Narcotic Combinations | 3 | $X,XXX | $10 |
| 04/05/2003 | Dr. MacArthur | Omeprazole | Proton Pump Inhibitors | 30 | $X,XXX | $10 |
| 03/23/2003 | Dr. MacArthur | Hydrochlorothiazide | Thiazides and Thiazide-Like Di | 30 | $X,XXX | $10 |
| 03/20/2003 | Dr. MacArthur | Warfarin Sodium | Coumarin Anticoagulants | 20 | $X,XXX | $10 |
| 03/20/2003 | Dr. MacArthur | Acetaminophen w/ Codeine | Narcotic Combinations | 2 | $X,XXX | $6 |
| 03/18/2003 | Dr. MacArthur | Warfarin Sodium | Coumarin Anticoagulants | 5 | $X,XXX | $10 |
| 03/15/2003 | Dr. MacArthur | Tramadol HCl | Narcotic Agonists | 7 | $X,XXX | $15 |
| 03/08/2003 | Dr. MacArthur | Ciprofloxacin HCl | FLUOROQUINOLONES | 30 | $X,XXX | $10 |
| 03/05/2003 | Dr. MacArthur | Omeprazole | Proton Pump Inhibitors | 90 | $X,XXX | $30 |
| 03/04/2003 | Dr. MacArthur | Losartan Potassium | Angiotensin II Receptor Antago | 30 | $X,XXX | $30 |
| 02/07/2003 | Dr. MacArthur | Esomeprazole Magnesium | Proton Pump Inhibitors | 90 | $X,XXX | $30 |
| 02/03/2003 | Dr. MacArthur | Levothyroxine Sodium | Thyroid Hormones | 7 | $X,XXX | $10 |
| 01/23/2003 | Dr. MacArthur | Methylprednisolone | Glucocorticosteroids | 10 | $X,XXX | $15 |
| 01/22/2003 | Dr. MacArthur | Clarithromycin | Clarithromycin | 6 | $X,XXX | $10 |
| 01/22/2003 | Dr. MacArthur | Codeine-Guaifenesin | Cough/Cold/Allergy Combination | 28 | $X,XXX | $10 |
| 01/09/2003 | Dr. MacArthur | Albuterol | Sympathomimetics | 30 | $X,XXX | $10 |
| 01/02/2003 | Dr. MacArthur | Esomeprazole Magnesium | Proton Pump Inhibitors | 15 | $X,XXX | $30 |
| 01/02/2003 | Dr. MacArthur | Pseudoephedrine-Guaifenesin | Cough/Cold/Allergy Combination | 30 | $X,XXX | $10 |
| 12/14/2002 | Dr. MacArthur | Esomeprazole Magnesium | Proton Pump Inhibitors | 30 | $X,XXX | $30 |
| 12/14/2002 | Dr. MacArthur | Acetaminophen w/ Hydrocodone | Narcotic Combinations | 2 | $X,XXX | $9 |
| 12/06/2002 | Dr. MacArthur | Losartan Potassium | Angiotensin II Receptor Antago | 90 | $X,XXX | $30 |
| 12/12/2002 | Dr. MacArthur | Esomeprazole Magnesium | Proton Pump Inhibitors | 30 | $X,XXX | $46 |

FIG. 11

SYSTEM AND METHOD FOR ADMINISTERING HEALTH CARE COST REDUCTION

CROSS-REFERENCE TO RELATED APPLICATIONS

This patent application is a continuation of copending U.S. patent application Ser. No. 10/813,968, filed Mar. 31, 2004, which is incorporated herein by reference in its entirety for all that it teaches.

FIELD OF THE INVENTION

The present invention provides for the efficient administration of health care plans, particularly as to the reduction and/or elimination of avoidable medical costs for select individuals who participate in the plan. The invention permits insurance plans to work with plan participants to optimize a health care regimen while simultaneously reducing the total benefit payouts by the plan, thus resulting in a more efficient delivery of health care services. Among other things, the invention provides case managers and health care providers with information relating to a plan participant's most pertinent health information, which in turn assists these individuals to efficiently identify and prioritize the candidates who would most benefit from case management. The information, including one or more scores or flags that reflect expected utilization of health care services and/or the desirability of an intervention in the health care regimen of a plan participant, is presented in a user-friendly format. In a preferred embodiment of the invention, the pertinent health information includes an indication as to whether an individual is predicted to make a disability claim.

BACKGROUND OF THE INVENTION

Health insurance plans pay out billions of dollars a year in benefits on behalf of insurance plan participants. Only a small portion of this expenditure, however, is directed to the use of lower cost preventive care to reduce potentially higher cost reactive care. In contrast to reactive health care, preventive health care identifies and reduces the causes of injury and/or illness. A preventive health care regimen, which may include screening for diseases and risk factors, physical examinations, vaccinations, and preventing complications of chronic diseases, may be implemented by health care providers. Health care providers, such as doctors, nurses and their assistants, choose tests, prescribe medicine, make referrals to specialists, counsel and/or use other techniques of proven utility in order to assist the treatment and/or recovery of an individual. Likewise, non-medical case managers can suggest alternatives, such as generic alternatives to name brand drugs, that do not require the advice of a medical professional. Case managers may also provide information to a participant who is unaware of alternative treatments.

Despite the well-documented and obvious benefits of preventive medicine, i.e. reducing unnecessary costs and improving the health of the plan participants, insurance companies that have implemented preventive plans have enjoyed only limited success. This was caused, at least in part, by the inability of case managers and health care providers to accurately identify the candidates within an insurance plan who would most benefit from intervention. In addition, prior art approaches failed to make relevant and useful information available to case managers and health care providers in an efficient and user-friendly manner.

Since the late 1960s, the health insurance industry has performed risk assessment on its insured and potential insureds, particularly for individual major medical insurance. Conventional risk assessment involves evaluating blood tests, analyzing attending physician statements, asking a series of medical history questions, and then applying established guidelines that determine whether a person is 25 percent higher cost risk, 50 percent higher cost risk, etc.

Risk assessment attempts to compensate for deficiencies in experience ratings by assigning risk levels to individuals or a group of enrollees. These risk levels are then used to project the expected costs of subgroups in a population. Existing risk assessment models use two types of data as expected cost predictors: demographic variables and health status. Demographic variables may include age, sex, family status, location, and welfare status, while health status measures can range from self-reported health assessments to requests for diagnoses and prior utilization of medical resources, such as hospitalizations. Models incorporating health status also usually include demographic variables as predictors of costs.

Actuaries have used risk assessment for years in the pricing of health insurance using techniques such as age/sex rating, experience rating, and tier rating. Tier rating is essentially a simplified version of experience rating generally applied to small group populations. Rather than each group having a unique rate based on experience, the experience is used to place that group into one of several "tiers," the higher-cost tiers reflecting higher historical claims and thus expected costs. HMO premiums for Medicare beneficiaries have also been risk adjusted for more than a decade using variables such as age, sex, geography, welfare and institutional status in a process known as the Adjusted Average Per Capita Cost ("AAPCC"). In more recent years, alternative risk assessment methods have been researched and developed, including models based on health status, as measured by utilization of medical resources and patient diagnoses. The federal government is currently exploring the use of health status measures as alternatives to the AAPCC. Under the umbrella of health care reform, several states have either begun risk adjustment or are in the process of implementing risk adjustment legislation. Risk adjustment refers to the transfer of funds from one plan to another, based upon the risk profile that is observed through risk assessment of all the plans, in an attempt to equalize the playing field among all plans and minimize incentive for avoidance of high-risk enrollees.

Other risk assessment methods include Ambulatory Care Groups ("ACGs"), Diagnostic Cost Groups ("DCGs"), Payment Amounts for Capitated Systems ("PACS"), self-reported health status measures, physiologic health measures, mortality patterns, prior use, the Robinson-Luft Multi-Equation Model, the New York State retrospective conditions/procedures payment method, and an elaborate method using marker diagnoses developed in California.

Risk assessment can be performed prospectively or retrospectively, and the risk adjustment process can also be performed prospectively or retrospectively. Generally, prospective risk assessment uses the experience of one year, such as 2001, to predict the risk attributes of an upcoming year, such as 2002. Prospective risk adjustment occurs when funds are transferred from insurers having relatively high risk profiles, as measured through prospective risk assessment, to those having relatively low (prospective) risk profiles. Prospective risk assessment is also applied in setting capitation rates for provider payment purposes Generally, each insurer builds the expected risk adjustment transfer amounts into their premium rates. A true prospective methodology implies that once the prospective assessments are used to determine transfers, there will be no ultimate transfer of funds based upon actual results. Thus, a true prospective methodology leaves intact a strong incentive to manage medical costs effectively, an incentive that might be removed by retrospective assessment as described below.

Retrospective risk assessment uses the experience of one year to determine the risk assessment attributes of that same year. Likewise, retrospective risk adjustment for a year implies the transfer of payments between carriers based on actual health care costs and risk assessed for that year. A retrospective settlement is an example of retrospective risk adjustment. A reinsurance system for large amount claims is another example of retrospective risk adjustment.

In summary, previous applications of risk assessment and risk adjustment have involved a range of approaches. Efforts by states have typically employed demographic factors such as age, gender, family size and geography, with some method of reinsurance or retrospective adjustment for high cost cases. The application of risk assessment methods in setting capitation payments, profiling providers and performing research on outcomes measurements has typically focused on using age and sex and in some cases, using diagnosis-based approaches such as ACGs and DCGs.

SUMMARY OF THE INVENTION

A system and method for administering health care cost reduction through the efficient use of interventions in an insurance plan participant's health regimen is disclosed. Information is processed and provided to case managers and/or health care providers in a manner that significantly improves the ability of such individuals to selectively identify those plan participants who are most likely to benefit from intervention. A customized database is built or extracted from a larger set of insurance data, and this data is then further processed to generate, based on prior claim and medical history, a score that reflects the relative desirability of an intervention in the participant's health care regimen. A participant may be identified as an intervention candidate based on claim history, the existence of one or more prior medical conditions, the prediction of a future medical event or insurance claim, or based upon a composite value in which constituent values represent prior conditions or claims.

According to one aspect of the invention, a prediction model is used in order to predict whether a plan participant will make a disability claim. Through empirical evidence, it has been determined that interventions are particularly warranted for those candidates with certain medical conditions and who are predicted to have a disability event. The likelihood of a disability claim is presented to case managers and/or health care providers as a flag. The case managers and/or health care providers are thus made aware that a particular candidate is suitable for an intervention.

In yet another aspect of the invention, an intervention candidate is selected based on a combination of factors. An information system processes health insurance data to create a first score, which is a predicted measure for the relative expected utilization of health services for the upcoming twelve months, and a second score, which is a value representative of the relative desirability of an intervention for the candidate. The information system further processes health insurance data to determine the status of one or more flags, each of which potentially indicates the relative desirability of an intervention in a plan participant's health care regimen. A predictive model is used to determine the status of a flag relating to the likelihood of an insurance plan participant making a disability claim within a certain period of time. Intervention candidates are thereafter selected based on a comparison of one or more scores with a threshold and/or the presence or absence of certain flags.

In a still further aspect of the invention, a case manager or health care provider accesses a complete suite of data regarding a suitable intervention candidate. The data is obtained from an information server that has the ability to access and display the candidate's data, which data may otherwise be spread across multiple disparate computers and databases. Information is presented to a case manager or health care provider via an Internet browser based graphical user interface. The case manager may monitor and input data relating to the intervention candidate and may further assign intervention candidates to a health care provider who will intervene in the health care regimen. Likewise, the health care provider may monitor and input data relating to the invention candidate.

BRIEF DESCRIPTION OF THE DRAWINGS

Exemplary embodiments of the invention are given below with reference to the drawings, in which:

FIGS. 5-11, inclusive, are screenshots of an exemplary user interface that interactively displays information to case managers and/or health care providers and further permits such individuals to input and update information.

DETAILED DESCRIPTION OF PREFERRED EMBODIMENTS

Figure 1:
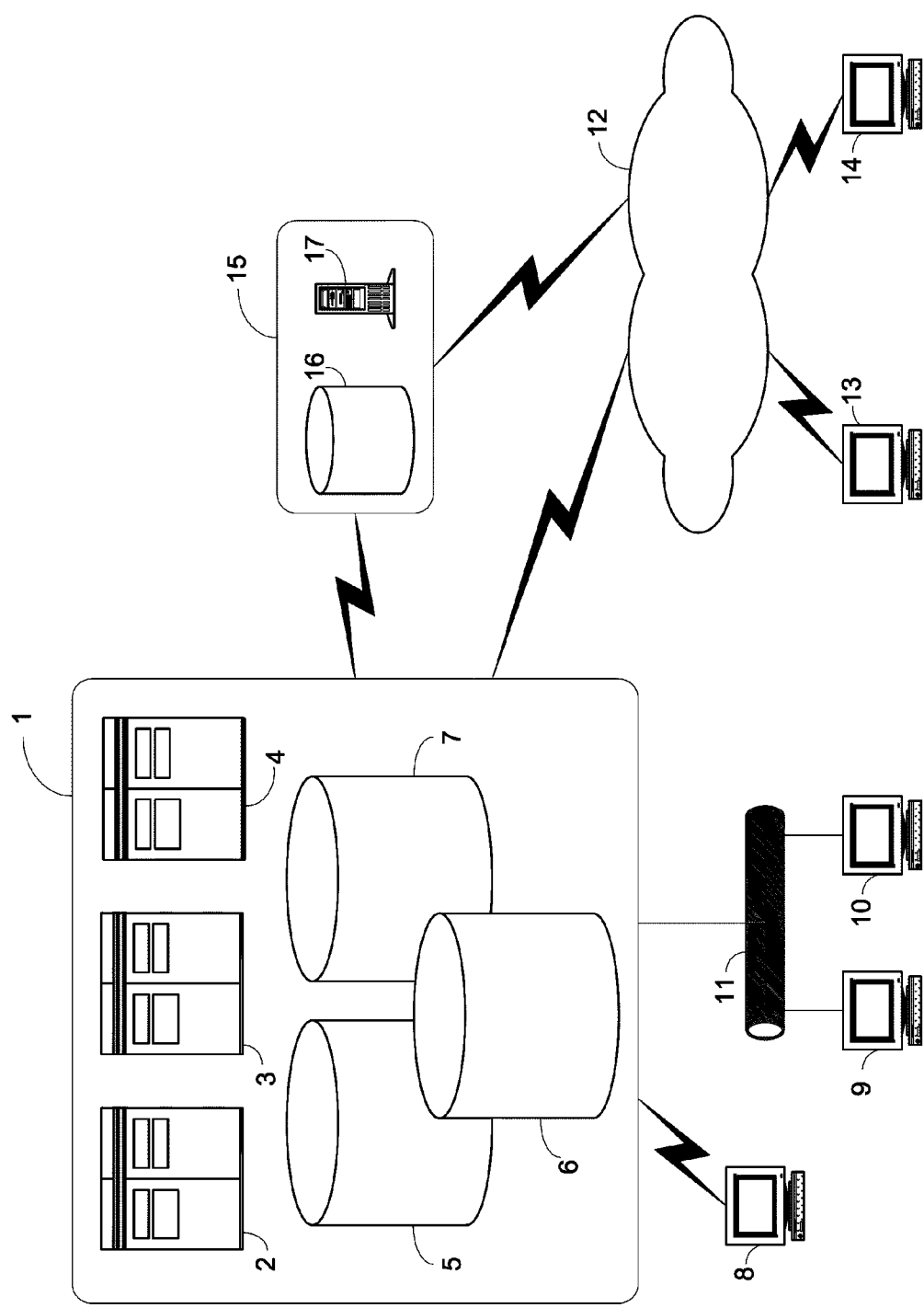
FIG. 1 is a schematic diagram of an exemplary environment in which the inventive system and method may be used to input, store, process, sort and display insurance information to case managers and health care providers.

FIG. 1 illustrates a logical arrangement of the environment in which the invention is useful. It will be understood by a person of skill in the art, however, that FIG. 1 is merely exemplary of a computer network environment in which multiple computers interconnect to a prior art insurance system 1. Accordingly, the illustration of FIG. 1 is not meant to limit the number and types of connections to the prior art insurance system 1.

In a manner described below, the data processing aspects of the present invention may be implemented, in part, by programs that are executed by a computer. The term "computer" as used herein includes any device that electronically executes one or more programs, such as personal computers (PCs), hand-held devices, multi-processor systems, microprocessor-based programmable consumer electronics, network PCs, minicomputers, mainframe computers, routers, gateways, hubs and the like. The term "program" as used herein includes applications, routines, objects, components, data structures and the like that perform particular tasks or implement particular abstract data types. The term "program"

as used herein further may connote a single program application or module or multiple applications or program modules acting in concert. The data processing aspects of the invention also may be employed in distributed computing environments, where tasks are performed by remote processing devices that are linked through a communications network. In a distributed computing environment, programs may be located in both local and remote memory storage devices.

Insurance system 1 processes and stores information relating to health insurance plans in a manner known in the prior art. Such a system includes, for example, data relating to the health care history and claim history of plan participants. The system 1 also processes and stores information that permits proper payment of claims made on behalf of plan participants. As illustrated in the exemplary environment of FIG. 1, insurance system 1 may include multiple interconnected computers 2-4 and databases 5-7. The number and type of computers 2-4 and databases 5-7 are selected to meet the needs of the insurance company that administers insurance plans. Large insurance databases may include several terabytes of data and several data processing computers.

Among other things, the insurance system 1 typically stores information for each plan participant or member. Member data includes, for example, name, member identification number, address, telephone number, age, date of birth, gender, geographic region, member's medical claims, member's pharmacy claims, primary care physician (if appropriate), a last discharge from case management date, a health profile (including diseases or conditions for which the member received treatment and associated dates), diagnoses, and information relating to specialists (including the specialty and date last seen). The insurance system also maintains and stores information relating to each plan. From this data, and using known statistical techniques, the insurance system 1 is able to calculate for each insurance plan participant a predicted measure for the relative expected utilization of health services for the upcoming twelve months. In a preferred embodiment, this data is known as a "PULSE" score, which is an acronym for Predicted UtiLization by Statistical Evaluation.

Data residing within insurance system 1 may be accessed, and additional data may be input, by directly connected computers, such as computer 8, or by other computers connected via a network, as is schematically illustrated by computers 9-10 and network 11. Although the exemplary environment of FIG. 1 illustrates only a single computer directly connected to the insurance system and only two computers connected via a network, it will be understood by a person of skill in the art that a large number of computers, whether networked or directly connected to one or more computers within the insurance system 1, will be used to access data within the system or to input new data. The data of insurance system 1 also may be accessed and input via remotely located computers, such as computers 13-14 and the Internet 12. The illustration of representative computers in FIG. 1 is not intended as a limitation on the number or types of communication with insurance system 1.

Insurance system 1 accepts, stores and acts upon data that is input by administrators and other authorized personnel. For example, information relating to insurance plans offered by the insurance company and information relating to the individual plan participants must be input to the system. Claims by medical providers and pharmacies also must be input to the system. Likewise, claims by individuals, such as disability claims, are input to the system. The programs and applications running on insurance system 1 use the input data to reconcile premiums, benefits and claims on behalf of plan participants and medical service providers.

The data processing aspects of the present invention further include an information system 15, which includes a database 16 and computer 17. It will be understood by a person of skill in the art that system 15 may be implemented either as a physically separate structure or as a logically separate structure. In a manner described in more detail below, information system 15 extracts data from the insurance system 1. Computer 17 and the programs running thereon include an Internet server application and an information server that is capable of accessing information on database 16. In a preferred embodiment, the Internet server application and the database application are supplied by SAS Institute Inc. of Cary, N.C. In this preferred embodiment, an SAS Internet module, "SAS/IntrNet," provides both Common Gateway Interface (CGI) and Java technologies for building Internet applications and data and compute services that allow users to access and execute remote SAS programs, such as those SAS programs used to create and manage database 16.

Figure 2:
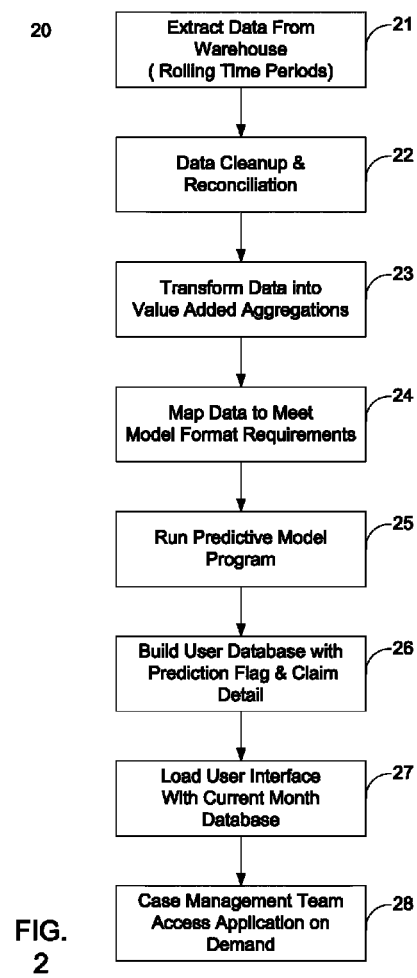
FIG. 2 is a block diagram representing the steps associated with the generation and processing of information that may be used to identify those participants/members in an insurance plan for whom a preventive health intervention would likely yield the greatest benefits.

FIG. 2 illustrates the steps, generally identified by reference numeral 20, associated with the generation of a subset of medical insurance information from the larger set of medical information contained on insurance system 1. This subset of information is used to identify and manage potential targets for reductions in medical costs. More specifically, an overall objective of the sequence of steps indicated by reference numeral 20 is the identification of those plan participants/members within an insurance plan for whom a preventive health intervention would likely yield the greatest benefits ("intervention candidate"). It is a further overall objective to present the relevant information relating to such candidates in a user-friendly interface. These objectives are accomplished via the database and programs running in conjunction with information system 15 that develop for each intervention candidate a plurality of flags and/or at least one "score" that indicates the relative desirability of an intervention for the candidate. The composite information, including claim history details, is thereafter presented to case managers and/or health care providers in a graphical user interface.

In step 21 of FIG. 2, information system 15 extracts data from the insurance system data warehouse, which is generally identified in FIG. 1 as databases 5-7. Information system 15 extracts only select data from the data warehouse of insurance system 1. In a preferred embodiment, the subset of data extracted from the data warehouse consists of claim and health information of those participants in an insurance plan whose expected utilization score exceeds a predetermined threshold. In this manner, only those members who are expected to incur substantial costs in the near future are examined for possible intervention. Other thresholds and/or criteria may be used to select the subset of data to be extracted. For example, a threshold monetary claim amount also may be used to select a subset of relevant candidates and/or data.

Extraction step 21 is conducted once every month. The frequency of data extraction, i.e., rolling time periods, depends on the need to update and maintain data in database 16. For example, an extraction frequency of one time per month is sufficient for a system wherein the underlying data set is updated only once monthly. After the data is extracted, information system 15 "cleans" the data by removing extraneous fields and information, and then reconciles the extracted data, step 22. The data is subsequently transformed into "value added aggregations," step 23. In this step, the data is combined into clinical and financially homogenous groupings, which is useful in establishing patterns that are subsequently used in the predictive modeling step.

Next, in step 24, the data is mapped to meet format requirements of a predictive model. As is known, a predictive model program is comprised of code that executes logic to determine whether certain events may occur. In a preferred embodiment, a model was created to predict the members most likely to have at least one disability claim in a certain calendar year based on their medical claims in the preceding calendar year. The model was built using logistic regression techniques (e.g., multivariate regression techniques) as applied to the historical medical and disability claims data for a large sample of individuals. More particularly, a utilization unit set appropriate for modeling the likely future disability event in the subject population was determined, a test production function (a formula, for example) using the utilization unit set that models the likely future disability event was assembled, and the test production function that describes the likely future disability event using at least one of financial data or clinical data associated with the likely future disability event was verified.

The predictive model was created through the iterative process of applying a multivariate regression analysis to a first clinical variable set that contains variables related to the likely future disability event and the subject population to produce first results. These results were analyzed to determine a first accuracy measure, which was subsequently compared against a results criteria to determine if the first accuracy measure has a predetermined relationship to the results criteria. A production function using the first variable set that models the likely future disability event in the subject population was used if the first accuracy measure had the predetermined relationship to the results criteria. When the first variable set yielded a less than desirable outcome, a second variable set was generated. The second clinical variable set also contains clinical variables related to the likely future disability event and the subject population. A second set of results were generated to determine a second accuracy measure, which was subsequently compared against a results criteria to determine if the second accuracy measure has a predetermined relationship to the results criteria. This process was continued until the creation of a suitable predictive model. In a similarly iterative fashion, a production function was modified as necessary to correct deficiencies identified in the verification step.

Separate predictive models for the likelihood of a disability claim were created for members with different types of health plans, e.g., HMO or PPO or Managed Choice coverage, and within HMO health plans, a separate model was further created for males and females in order to increase predictive accuracy when compared with a combined sex model. The input to this model are various medical claim values for a particular individual for a particular year, and the output, i.e., the output of step 25, is a binary "yes" or "no" prediction of whether or not the individual will have at least one medically based disability claim in the following year. The output, however, could also be a numerical indicator of the probability of such claim. For example, a twenty-five percent (25%) likelihood of a disability claim for the following twelve (12) month period could be reported as such rather than a simple "no."

Due to the fact that data may be maintained in disparate formats, and due to the existence of multiple models, it is necessary to determine which map format applies to the relevant data and to actually map the data to meet the requirements of the model, step 24. Information system 15 thereafter executes the predictive model program, step 25, and stores the results as part of the database that is built by information system 15 in step 26. This database, such as database 16, includes claim history and other related information as described above.

An important part of the overall objective of the sequence of steps 20, which is particularly indicated in step 26, includes the generation of a separate metric or "action score," which is intended to be used primarily for determining the relative desirability of an intervention in the health care regimen of a plan participant. The action score thus may be distinguished from the expected utilization score, which predicts the relative consumption of health care services regardless of whether such consumption may be altered through an intervention. Although it provides different information from the expected utilization score, the action score, like the expected utilization score, depends on the intervention candidate's prior consumption of certain health care services.

In one preferred embodiment, the action score is an integer that is generated by adding several values, each of which represents the intervention candidate's consumption of a different health care service. A first component of the action score is a value that represents a count of unique specialty types encountered in medical claims or encounters for the intervention candidate over the last 12 months. The second component is a value that represents the number of inpatient admissions for the intervention candidate over the last 12 months. The third component is a value that represents the number of diseases or conditions for which the candidate sought treatment. A fourth component is a value that represents the number of unique drug prescriptions, as determined, for example, at the generic drug name level. A fifth component is a value that represents the sum of allowed amounts for all medical claims incurred over the prior six (6) months. A sixth, and final component in a preferred embodiment, is the number of emergency room visits for which the intervention candidate was not admitted. The following table provides an example of the values representing the foregoing components:

TABLE ONE

| Action Score Component | Range of Values |
| --- | --- |
| Count of specialists | 0-3 specialties = 0 points |
|  | 4-5 specialties = 1 point |
|  | 6-7 specialties = 2 points |
|  | 8+ specialties = 3 points |
| Inpatient admissions | 0 admits = 0 points |
|  | 1 admits = 1 point |
|  | 2 admits = 2 points |
|  | 3+ admits = 3 points |
| Count of chronic diseases | 0 diseases/conditions = 0 points |
|  | 1 diseases/conditions = 1 points |
|  | 2+ diseases/conditions = 2 points |
| Unique prescriptions count | 0-8 drugs = 2 points |
|  | 9+ drugs = 3 points |
| Medical claims allowed | $0-$5000 = 0 points |
|  | $5001-$20000 = 1 points |
|  | $20001+ = 2 points |
| Emergency room visits (without admit) | 0-2 ER visits = 0 points |
|  | 3 ER visits = 1 points |
|  | 4+ ER visits = 2 points |

Although these values and components are used in a preferred embodiment, it will be readily obvious to persons of skilled in the art that different components and/or values could be used to compute the action score. For example, fractional or decimal values instead of integers could be used. Likewise, rather than merely adding component values, the action score could be determined based on a weighted matrix in which certain components are weighted more heavily or less through the use of an appropriate scaling factor. Finally, persons of skill in the art may determine that other components may be useful in determining the action score. Biographical data, such as the patient's age, and/or related medical data, such as the intervention candidate's likelihood of developing a particular medical condition, could also be used in determining an action score. The foregoing, therefore, should not be interpreted as a strict protocol upon which an action score is determined. Instead, it is provided merely as an example of an algorithm, developed through empirical research, for determining an action score.

The database that is built in step 26 further includes the underlying data used to create the action score. In addition, the database includes sorted and categorized data, such as whether the candidate's last inpatient treatment facility was a participating or non-participating service provider, as well as "flags" that are readily useable to a case manager or health care provider who may seek to intervene in the candidate's health care regimen. A flag will typically indicate the presence or absence of consumption of a specific health care service or product. In addition, a flag may indicate the likelihood of an occurrence, such as a disability claim as determined in connection with step 25. In the preferred embodiment, information system 15 tracks the flags indicated in table two:

TABLE TWO

| Flag | Status/Explanation |
| --- | --- |
| Skilled Nursing Facility (SNF) Treatment | A yes/no indicator explaining whether there is evidence of treatment by a skilled nursing facility as determined from medical claims for the member over the last six (6) months. |
| Home Health (HH) Care | A yes/no indicator explaining whether there is evidence of home health care as determined form medical claims for the member over the last 12 months. |
| Disease Managed | A yes/no indicator explaining whether there is evidence of highest weight which is eligible for disease management. |
| Expensive Drugs | A pair of yes/no or N/A indicators determined through pharmacy claims paid through the medical claims system indicating whether the intervention candidate: (1) had a prescription for potentially expensive inject able drugs, and (2) whether the drugs were purchase through potentially cost-saving providers. |
| Disability | A yes/no indicator explaining whether there is evidence that the intervention candidate may make a disability claim within the next twelve (12) months. |

As with the action score components, it will be understood by persons of skilled in the art that different flags could be used. The foregoing flags are provided as examples, developed through empirical research, for use in a preferred embodiment. These flags, when combined with an expected utilization score and/or the action score, may be used by case managers and/or health care providers to quickly identify the intervention candidates who would most benefit from a health care regimen intervention.

In an alternative embodiment, the action score is not computed through the addition of the values representing an intervention candidate's consumption of a different health care service. Instead, in this alternative embodiment, the action score reflects only the existence of one or more of the conditions noted above in Table One or the status of flags noted in Table Two. In other words, all such values in this alternative embodiment are treated equally and an intervention candidate will be selected based on the existence of even a single out-of-range value or a certain flag, such as the disability flag.

Following the completion of the database, the user interface is loaded with all relevant data, step 27. Thereafter, the case management team is able to access the database on an as-needed basis via the Internet, step 28. Through the use of a graphical user interface, the case management team, including administrative case managers and health care providers, have access to the most timely and pertinent information that is needed to determine whether an intervention in a health care regimen is warranted, and if so, the nature of the intervention.

Figure 3:
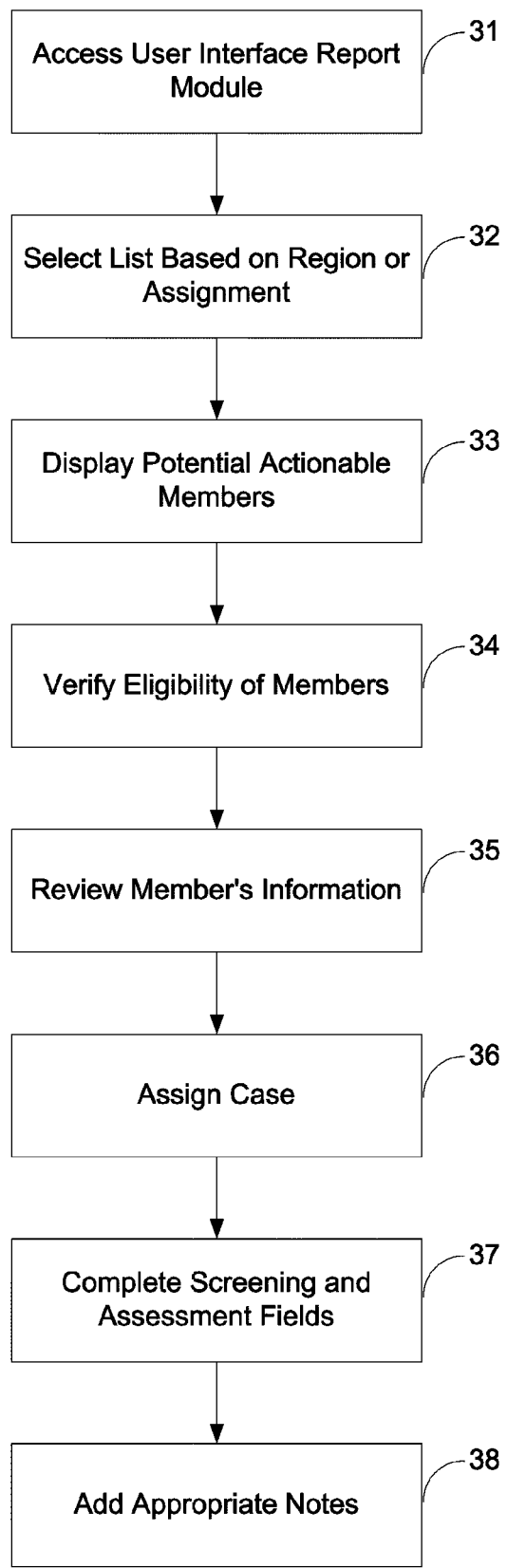
FIG. 3 is a block diagram of the manner in which a case manager or health care provider may access, input, process and/or use the information generated as a result of the process indicated in FIG. 2.

FIG. 3 indicates the steps 30 that may be undertaken by a case manager to assign an intervention candidate to a health care provider once the relevant database is built and made available via information system 15. The case manager accesses an interface report module, step 31, which is presented to the case manager or health care provider via an Internet connection and an Internet browser application running on a client computer. The client computer may include more than a browser application, however. It may include applications that validate and/or verify data independently of the server application. The Internet server application on information system 15, however, supplies most of the health information displayed on the client computer.

The case manager selects a list of intervention candidates based on a geographical region of the country or a preexisting assignment list, step 32. In response to this selection, the information system server displays a list of potential "actionable" plan members, who are the candidates for whom a preventive intervention may result in favorable results, step 33. In a preferred embodiment of the invention, information system 15 returns a list of actionable plan members, which list is composed of only those plan participants whose expected utilization score exceeds a certain threshold and whose action score also exceeds a certain threshold. In a highly preferred embodiment, the threshold for an expected utilization score generally corresponds to the value that is assigned to the ninety-eighth percentile of plan participants. In other words, the list includes only those participants whose expected utilization score is greater than that of ninety-eight percent of all other participants. The threshold value itself is not expressed as a percentage; it is instead expressed as the real number that corresponds to the ninety-eighth percentile. Likewise, the threshold for the action score generally corresponds to the value that is assigned to a suitably "high" percentile of plan participants who receive the same or higher action score. The threshold values, of course, may be adjusted in order to select an appropriate number of candidates. Information system 15, however, typically will not return as eligible those participants who are already active in the case management system.

The case manager next determines the eligibility of the actionable members, step 34. This step is necessary because plan participants may drop out and/or terminate their participation in the plan. The case manager also reviews the plan participant's information to determine the suitability for a case management intervention, step 35. Once the case manager has determined that a plan participant is a suitable candidate for intervention, the case is assigned to a health care provider, step 36. The case manager also completes relevant inquiries as to screening information for the intervention candidate, step 37, and further adds to the electronic file any appropriate notes, step 38.

Figure 4:
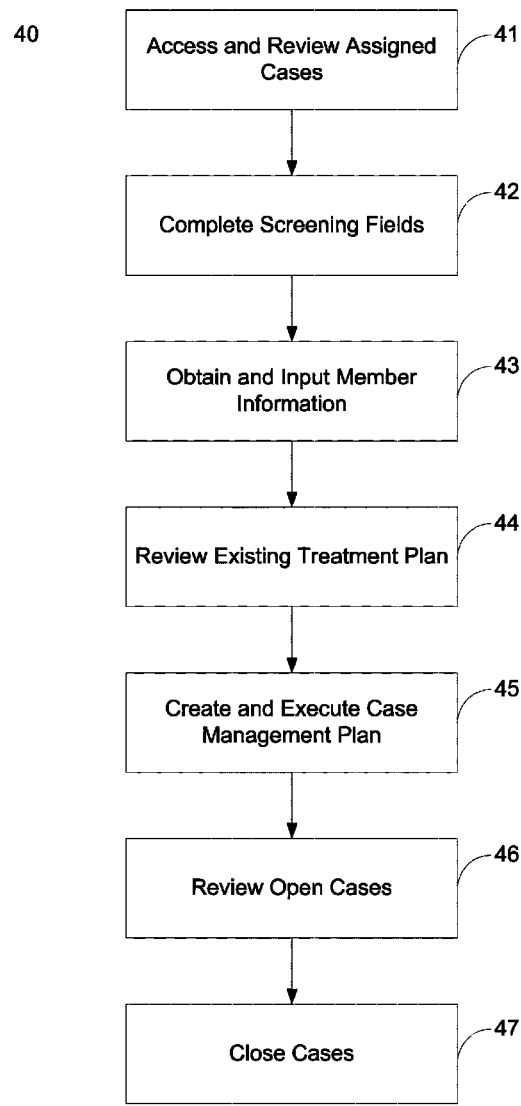
FIG. 4 is a block diagram of the manner in which a health care provider may access, input, process and/or use the information generated as a result of the process indicated in FIG. 2.

FIG. 4 illustrates typical steps 40 that a health care provider may encounter in processing assigned cases. In a first step, step 41, the health care provider accesses and reviews assigned cases. This step includes a review of the participant's demographics and case management history, summary information pertaining to medical and pharmacy information, the nature of treating specialists and other diagnostics information. The health care provider further completes all appropriate fields to complete screening for case management, such as the case management start date, step 42.

The health care provider next makes contact with the participant, step 43, to obtain information. In a preferred embodiment, the health care provider uses condition specific or generic assessment tools in order to identify any barriers to optimal health in seven domains: physiologic, functions, environment, support system, economic, cognitive, and psychosocial. At this point in time, it is desirable that the health care provider advise the intervention candidate regarding the benefits of preventive care, and, further, of the confidentiality aspects of the program. The health care provider also makes contact with a physician or the primary care physician, if necessary, in order to review the existing health care regimen, if any, and to determine the prognosis of the case, step 44.

In conjunction with a physician and the participant, the health care provider thereafter intervenes in the current health care regimen of the participant and determines a revised and customized case management selection plan that addresses the specific actionable issues, step 45. This plan takes into account the information and flags made readily available through information system 15. The plan includes as appropriate referrals to a twenty-four hour nurse line, a mail order pharmacy, Internet web tools/resources, disease management specialists, behavioral health specialists, providers that offer amenities at a discount, and transplant specialty teams. The plan also may include steps to address educational and cognitive deficits and/or steps to address episodic and long term functional and clinical needs, including preventive care and self monitoring and reporting. Finally, the health care provider together with the participant establishes short and long term case management goals.

Health care providers are assigned to multiple intervention candidates, and as such, routinely review "open" case management cases, step 46. In this review process, the health care provider works to accomplish short term case management goals and to insure that physical and provider needs are addressed. The review process further includes encouragement of successful self monitoring, reporting and follow up, and to assist where appropriate in providing preventive care.

Finally, health care providers will close cases after case management goals are met, step 47. In this step, the health care provider will work with both the participant and a physician. The health care provider will also provide the participant with a case manager name and telephone number in the event that additional action is required.

FIGS. 5-11, inclusive, are screenshots of an exemplary user interface that interactively displays information to care managers and health care providers and further permits such workers to input and update information. The user interface is presented via an Internet browser that obtains data over the Internet (or an internal network), which data is provided by information system 15. The screen shots illustrate various pages of information that may be displayed after a user has been properly authenticated and/or granted access to the server that provides the information. In addition, the illustrations in FIGS. 5 through 11 do not indicate any encryption of information, but it is expected that health insurance information transmitted over a public network will be encrypted. As such is well known in the art, it is not described further herein.

Figure 5:
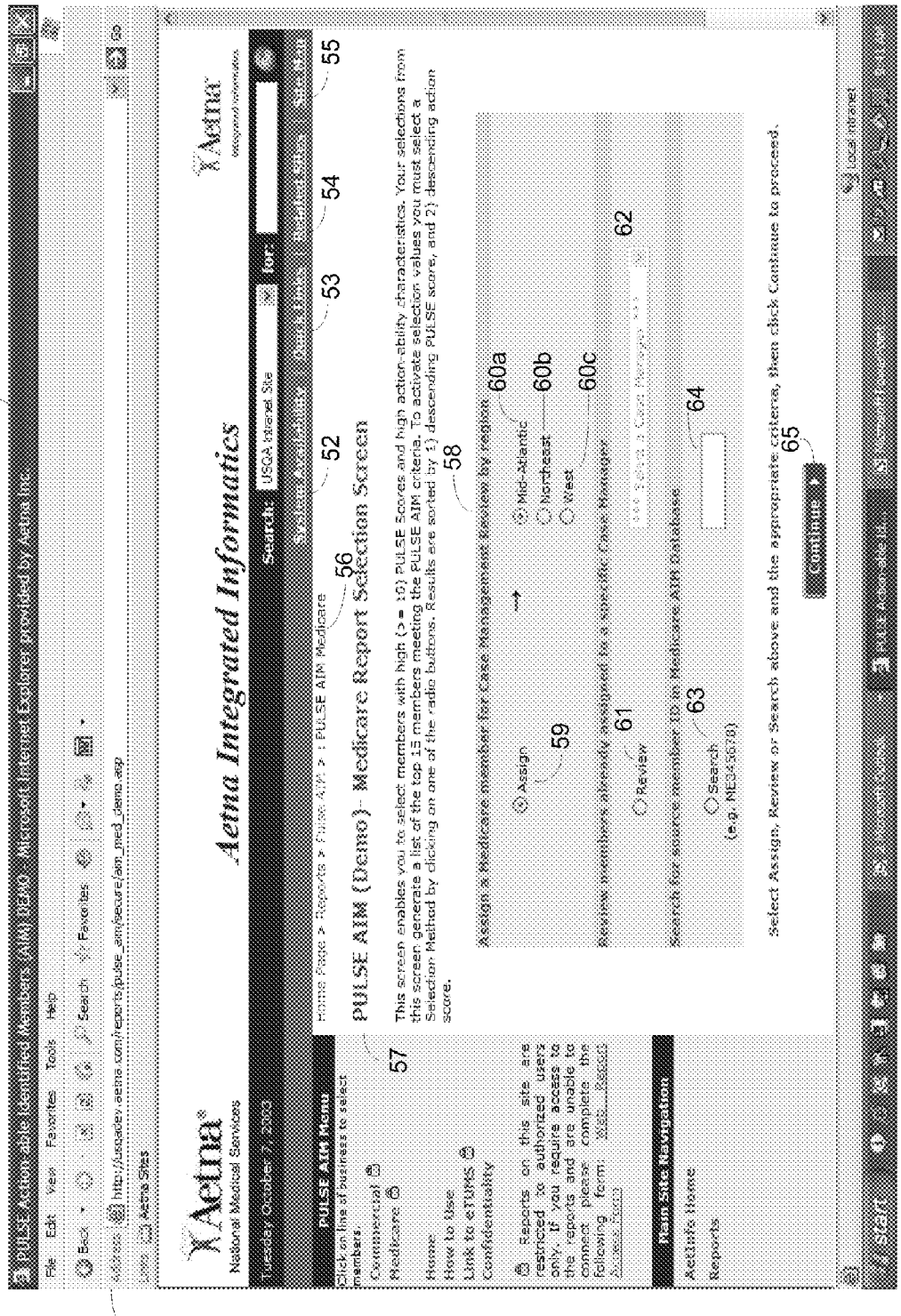

FIG. 5 illustrates a browser window 50 that displays a health insurance report selection screen, as indicated by title 57. A case manager accesses this page by entering an appropriate uniform resource locator (URL) in the browser address line 51. The browser further includes navigation links 52-55 and an indication 56 as to the location of the report page with respect to the home page of the site. FIG. 5 illustrates the first page that a case manager would access in order to assign an intervention candidate to a health care provider. FIG. 5 is exemplary of a screen display than an operator may encounter in performing steps 31 and 32 of FIG. 3, which are described above. The operator may select an option presented in dialog box 58 by choosing button 59 to select a region of the country, 60a-60c, button 61 to review a specific member (plan participant or intervention candidate) through drop-down menu 62, or button 63 to search for a specific member through fill-in box 64. Once the appropriate selection is made, the case manager clicks the "continue" button 65.

Figure 6:
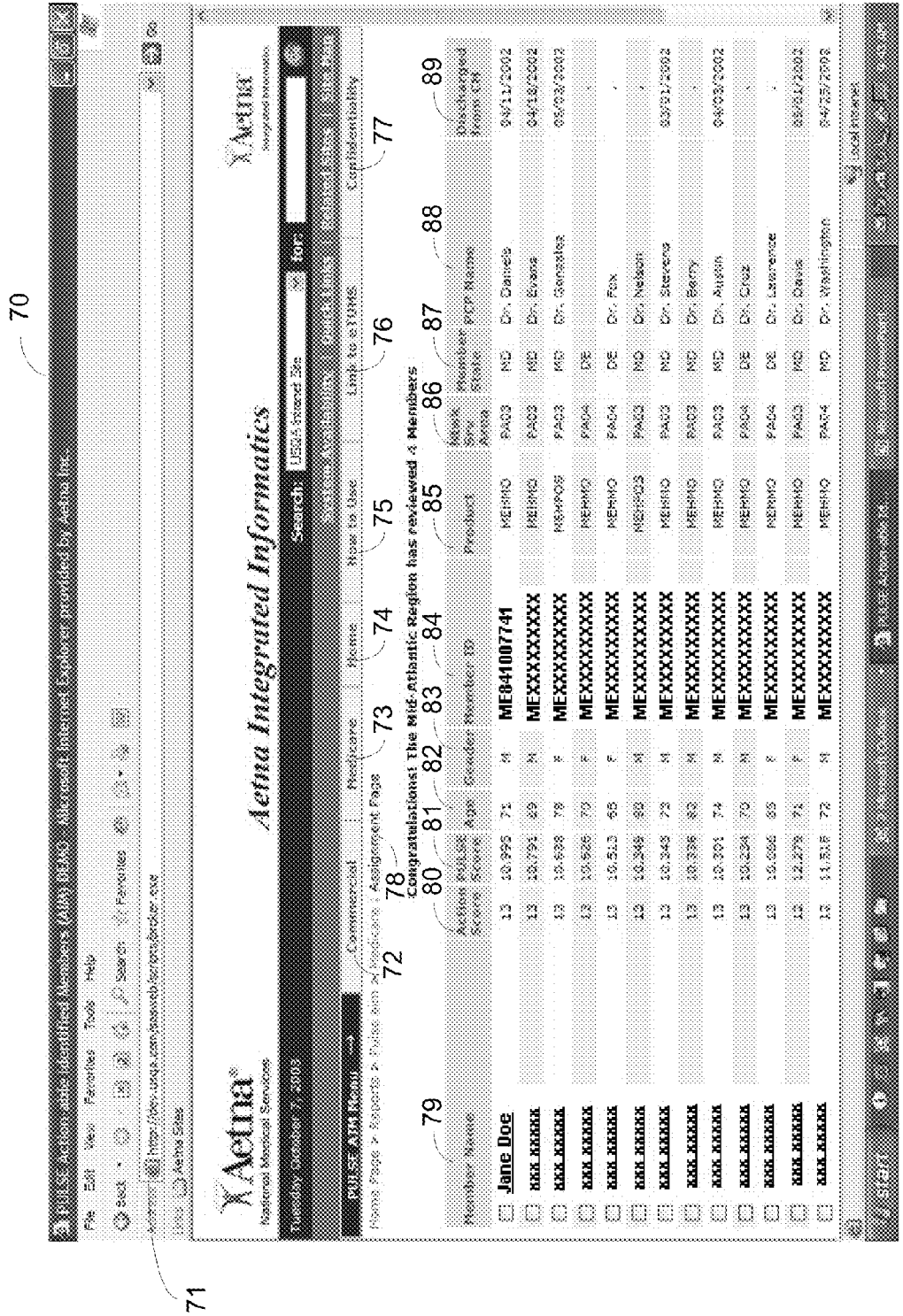

FIG. 6 illustrates a browser window 70 that displays a list of potential intervention candidates. This displays is exemplary of a display than an operator may encounter in performing step 33 of FIG. 3, which is described above. As with FIG. 5, the browser includes navigation links 72-77 and an indication 78 as to the location of the page with respect to the home page of the site. This exemplary page may be reached through the input of an appropriate URL in the browser address line 71. Alternatively, this page may be reached automatically via a web server in response to a user's prior selections.

In the illustration of FIG. 6, the browser displays several fields of relevant information, many of which are self-explanatory, including the member name 79, age 82, gender 83, member ID 84, member state 87 and primary care physician name 88. Other displayed information further includes the "product" 85, which identifies whether a plan is a PPO or HMO for example, and the network service area 86, which corresponds to a select geographic area of the country. Notably, information system 15 also returns information relating to relative desirability of an intervention for the candidate, the "action score" 80, as well as the predicted measure for the relative expected utilization of health services for the upcoming twelve months, the "PULSE score" 81. This information, as described above, is used to determine the relative desirability of intervening in a particular plan participant's health care regimen. Finally, the information displayed on this screen indicates the discharge status 89 for each candidate with respect to a case management plan.

Figure 7A:
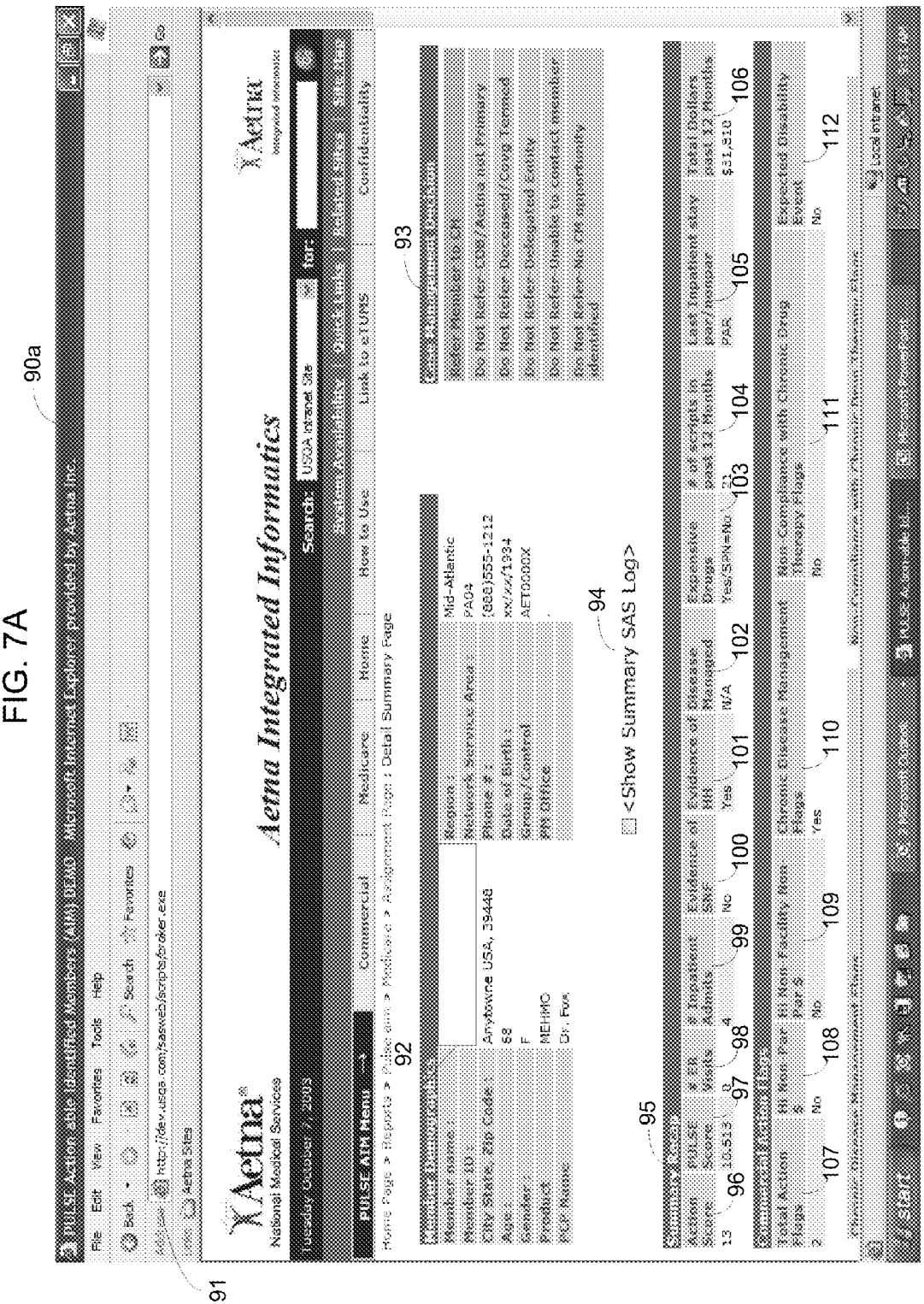
Figure 7B:
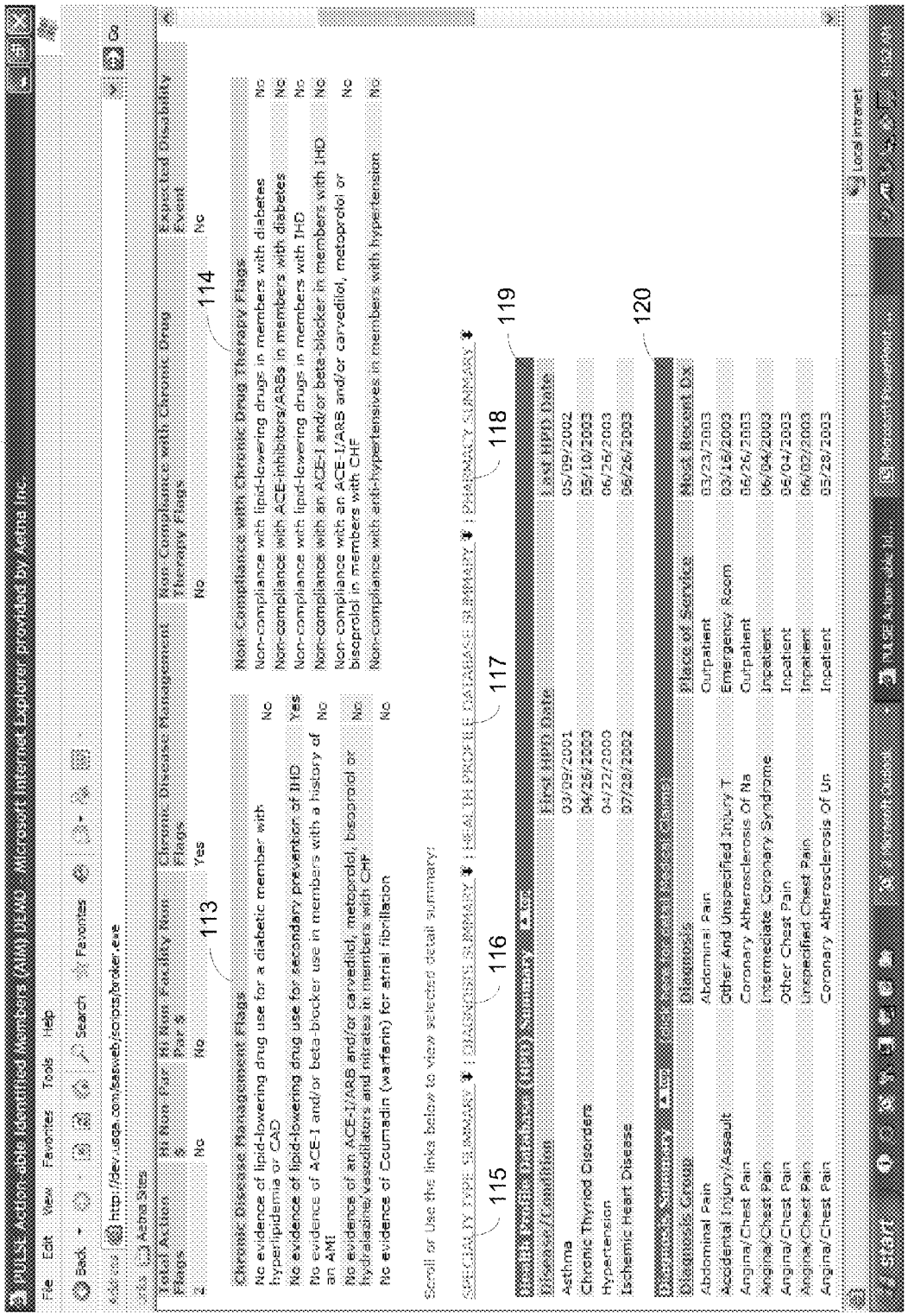
Figure 7C:
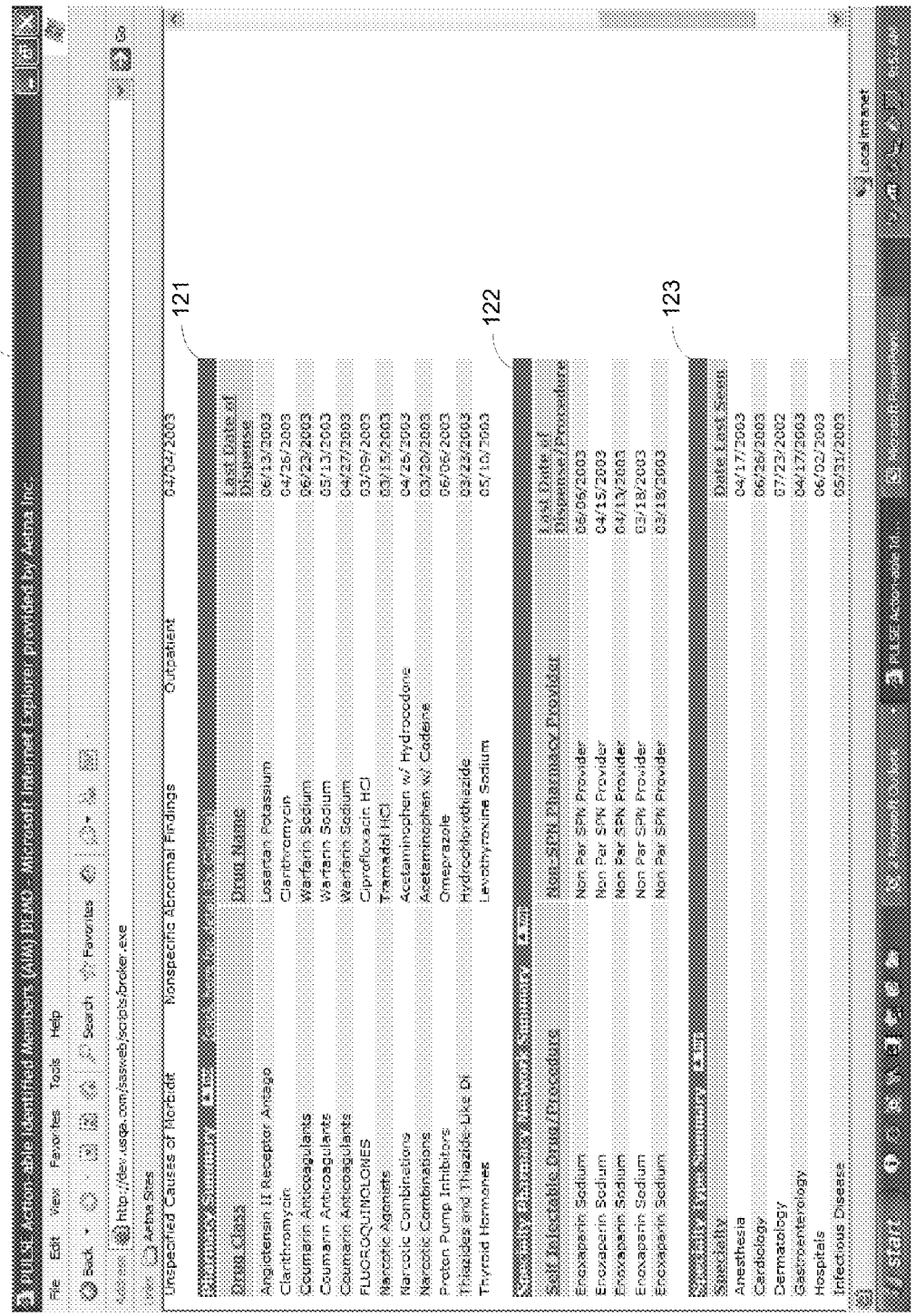

FIGS. 7A-7C illustrate browser windows 90a, 90b, and 90c, each of which displays a detailed summary of a particular plan participant's health and claim information. This information, again supplied by information system 15, is particularly helpful to a case manager or health care provider in reviewing the desirability of a particular intervention. It further reduces the need for the case manager or health care provider to access disparate systems. Instead, information system 15 provides all or substantially all of the relevant information needed to formulate an efficient case management plan. As particularly illustrated in FIG. 7A, a summary of the member (plan participant or intervention candidate) demographics 92 is displayed in a page reached through a URL 91. Likewise, an indication of the status of any case management decisions 93 is also displayed in a conspicuous manner. The display of detailed summary information including a "Show Summary SAS Log" 94 further includes a recap 95 of several relevant indicators including: action score 96, PULSE score 97, the number of ER visits 98, the number of inpatient admits 99, evidence of treatment in a skilled nursing facility 100, evidence of use of home health care 101, disease management 102, a status indicator as to the use of expensive drugs 103, the number of prescriptions over the past twelve (12) months 104, an indication as to whether the last inpatient stay was with a participating provider or a non-participating provider 105, and the total claims (in dollars) allowed over the past twelve (12) months 106. In addition, the detailed summary information includes a count of action flags 107, and the status of several action flags including whether a large amount of claims have been made for a non-participating provider, flag 108, or a non-facility and non-participating provider, flag 109. The information further includes whether there has been sufficient treatment for chronic diseases to set flag 110, whether the member has not sufficiently complied with chronic drug therapy to set flag 111, and whether there is a sufficient expected disability event to set flag 112.

FIGS. 7B and 7C, which are continuations of the same window as illustrated in FIG. 7A, further provides an indication of flags 113 relating to chronic disease management and flags 114 relating to non-compliance with chronic drug therapy. In order to access further health information, the window includes a series of navigation links 115-118, which permit the case manager and/or health care provider to select summaries such as a health profile database summary 119 (FIG. 7B), a diagnosis summary 120 (FIG. 7B), a pharmacy summary 121 (FIG. 7C), a specialty pharmacy network summary 122 (FIG. 7C), and a specialty type summary 123 (FIG. 7C). Other detailed summary information relating to the participant is also available on demand from information system 15.

It is noted, however, that information system 15 supplies more than summary information. The system tracks and provides detailed information as to prior claims and medical diagnoses. As illustrated in FIG. 8, browser window 130, which is accessed through URL 131, displays detailed medical claims information 132. Likewise, as illustrated in FIG. 9, browser window 150, which is accessed through URL 151, displays detailed pharmacy claim detail 152. The medical claim detail 132 (FIG. 8) includes information such as date of claim 133, place of service 134, the health care provider 135, the specialty of the provider 136, the primary diagnosis 137, the completed procedure 138, the allowed amount of the claim 139, the copayment 140, and whether the treatment was conducted by a participating or non-participating provider 141. The pharmacy claim detail 152 (FIG. 9) includes information such as date of claim 153, the prescribing provider 154, the product name 155, the drug class 156, the number of days supply 157, the paid amount of claim 158, and whether any copayment was made 159. Although only two detail screen shots are provided, FIGS. 8 and 9, it will be understood by persons of skill in the art that numerous additional detail screens relating to a participant's health information are possible and desirable.

Summary information, as illustrated in the exemplary displays of FIGS. 7A-7C, and detail information, as illustrated in the exemplary displays of FIGS. 8 and 9, supply case managers and health care providers with an integrated view as to the relevant claim and medical data. The summary claim and medical information, along with action scores and flag information in order to identify those intervention candidates who would most benefit from a health care regimen intervention, permits a more targeted and efficient intervention than was known in the prior art. The detailed information permits the case managers and health care workers with ready access to information that otherwise may exist on disparate systems and databases. The user interface thus allows the user to start at a summary level and thereafter drill down to obtain the information needed to formulate the most effective case management plan for suitable intervention candidates.

Figure 10:
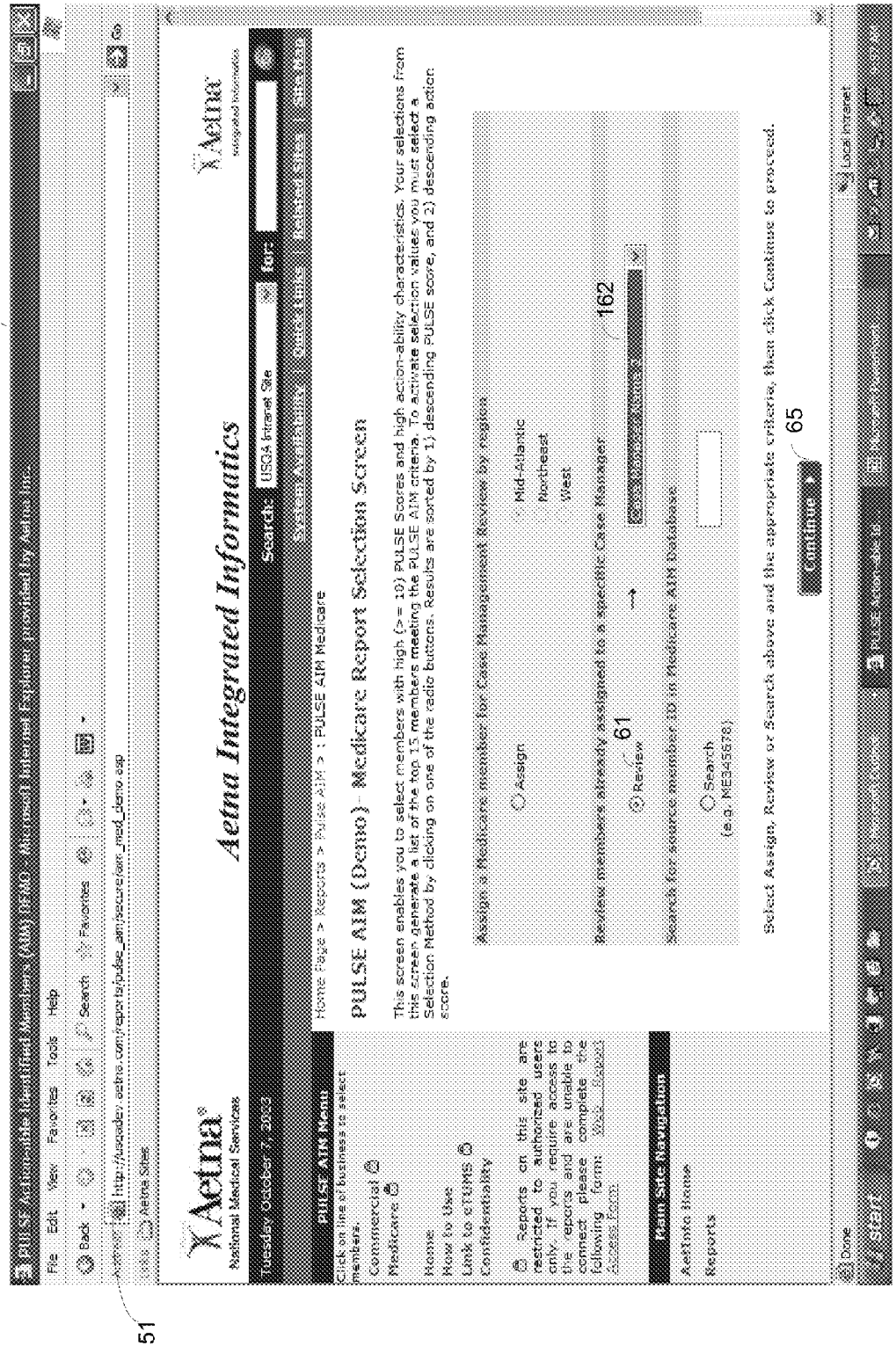

FIG. 10 illustrates a browser window 160 that displays a health insurance report selection screen. This browser window is similar to that illustrated in FIG. 5 (and is reached by the same URL in address line 51). In the exemplary illustration of FIG. 10, however, the user has selected the review option as indicated by button 61. FIG. 10 is exemplary of a screen display than an operator may encounter in performing a review step 46 of FIG. 4, which is described above. After selecting this option, by choosing a case manager (or health care provider) from the drop down selection box 162, and then clicking the "continue" button 65, a user is presented with a browser display such as that illustrated in FIG. 11.

Figure 11:
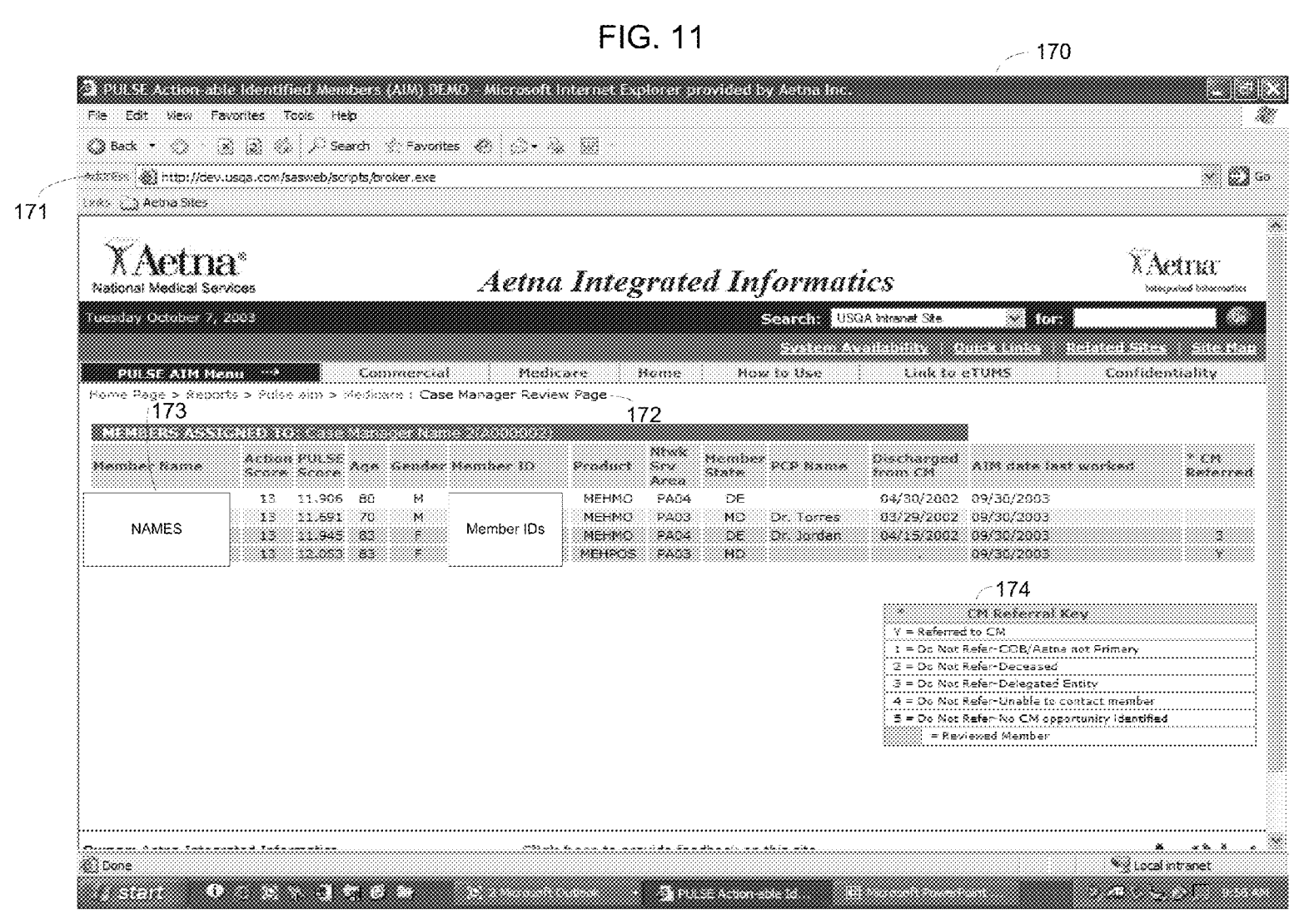

FIG. 11 specifically illustrates a browser window 170 that displays those intervention candidates 173 who have been assigned to a particular case manager or health care provider. As with other displays, this page is reached through an appropriate URL at address line 171. In addition, an indicator 172 provides the user with information as to the location of the page with respect to the site's home page. As is readily evident from the screen shot, the information in this display includes several items previously discussed. In addition, this display includes a "referral" key 174 that allows the user to code and decode the information in a case management field. Through the use of a graphical user interface as that illustrated in the exemplary screen shot of FIG. 11, a case manager may review open cases and/or close cases, as in steps 46 and 47 of FIG. 4, respectively.

While the invention has been described with an emphasis upon particular embodiments, it should be understood that the foregoing description has been limited to the presently contemplated best mode for practicing the invention. It will be apparent that various modifications may be made to the invention, and that some or all of the advantages of the invention may be obtained. Also, the invention is not intended to require each of the above-described features and aspects or combinations thereof. In many instances, certain features and aspects are not essential for practicing other features and aspects. The invention should only be limited by the appended claims and equivalents thereof, since the claims are intended to cover other variations and modifications even though not within their literal scope.

What we claim is:

1. A method for administering reductions in health care costs for those participants in a health insurance plan for whom future health care costs may be reduced through intervention ("intervention candidates") comprising computer implemented steps of:

extracting from a database participant data for each of a plurality of participants in the health insurance plan, the participant data comprising claims data representing at least one past claim, the past claim being one of a medical claim and a pharmacy claim, wherein: (a) the claims data representing the medical claim represents one or more of a procedure physically performed on or in connection with the participant, and a diagnosis of a disease or condition physically afflicting the participant, and (b) the claims data representing the pharmacy claim represents at least in part a drug physically administered to the participant;

executing a predictive model program using the participant data to generate an output, the predictive model program comprising computer executable instructions for determining a likelihood of occurrence of at least one predetermined future event, the event associated with utilization of health care services, the predictive model having been created using historical claims data from a sample of individuals, the predictive model program being stored on a non-transitory computer readable medium of at least one information server connected to the database;

determining, from the output of the execution of the predictive model program, via the at least one information server, a first score for an intervention candidate using the participant data, which first score reflects a predicted utilization of future health care services;

determining, via the at least one information server, a second score for the intervention candidate using the participant data, which second score is a function of the extent of the intervention candidate's prior consumption of a plurality of different predetermined health care services over a predetermined time interval, the second score reflecting relative desirability of intervention in a health care regimen of the intervention candidate;

comparing, via the at least one information server, the first score against a first threshold value and the second score against a second threshold value to identify at least one intervention candidate eligible for intervention and generating a result of such comparison and;

presenting a graphical user interface for providing to a select individual electronic access to a health care history of the at least one eligible intervention candidate and the result of the comparison, the graphical user interface including a display of historical information based at least in part on the participant data associated with the at least one eligible intervention candidate and adapted to facilitate intervention in the health care regimen of the at least one eligible intervention candidate based on the result of the comparison, wherein the second score is determined based on a weighted set of values, each value associated with a corresponding scaling factor and representing the intervention candidate's consumption of at least one of the plurality of different predetermined health care services.

2. The method of claim 1, wherein the second score is detei mined by adding a plurality of values, each value representing the intervention candidate's consumption of at least one of the plurality of different predetermined health care services.

3. The method of claim 2, wherein one of the plurality of values is selected from the group consisting of: a value representing a number of medical specialists that treated the candidate, a value representing a number of inpatient admissions, a value representing a number of chronic diseases for which the candidate was treated, a value representing a number of prescriptions for unique drugs, a value representing an amount of medical claims allowed, and a value representing a number of emergency room visits without admission in a hospital.

4. The method of claim 1 wherein at least one of the plurality of different predetermined health care services is selected from the group consisting of:
a unique drug prescription;
an instance of an inpatient admission;
an existence of a chronic disease or condition;
a unique medical specialty consultation;
an allowed medical claim exceeding a predetermined monetary threshold; and
an emergency room visit.

5. The method of claim 1, wherein one of the plurality of values in the matrix is selected from the group consisting of: a value representing a number of medical specialists that treated the candidate, a value representing a number of inpatient admissions, a value representing a number of chronic diseases for which the candidate was treated, a value representing a number of prescriptions for unique drugs, a value representing an amount of medical claims allowed, and a value representing a number of emergency room visits without admission in a hospital.

6. The method of claim 1, wherein the step of generating a result includes generating a first result that indicates whether the first score exceeds the first threshold value, a second result that indicates whether the second score exceeds the second threshold value, and a composite result that represents both the first and second results.

7. The method of claim 1, wherein the graphical user interface facilitates intervening by displaying the result of the comparison that causes a health care provider to contact the at least one eligible intervention candidate in order to recommend a change in the at least one eligible intervention candidate's health care regimen.

8. The method of claim 1 wherein the at least one information server is configured for generating a plurality of flags, wherein each flag has a status that represents the participant data associated with the intervention candidate.

9. The method of claim 8, wherein one of the plurality of flags represents the likelihood that an intervention candidate will claim disability under a disability insurance plan.

10. The method of claim 1, wherein the second score further indicates the potential for health care cost reduction of the intervention candidate as determined relative to other participants in the health insurance plan.

11. A method for administering reductions in health care costs for those participants in a health insurance plan for whom future health care costs may be reduced through intervention ("intervention candidates") comprising computer implemented steps of:

extracting from a database participant data for each of a plurality of participants in the health insurance plan, the participant data comprising claims data representing at least one past claim, the past claim being one of a medical claim and a pharmacy claim, wherein: (a) the claims data representing the medical claim represents one or more of a procedure physically performed on or in connection with the participant, and a diagnosis of a disease or condition physically afflicting the participant, and (b) the claims data representing the pharmacy claim represents at least in part a drug physically administered to the participant;

determining, via an information server connected to the database, an action score for the intervention candidate using the participant data, which action score is a function of the extent of the intervention candidate's prior consumption of a plurality of different predetermined health care services over a predetermined time interval, the action score reflecting relative desirability of intervention in a health care regimen of the intervention candidate;

comparing, via the information server, the action score against a threshold value to identify at least one intervention candidate eligible for intervention and generating a result of such comparison and;

presenting a graphical user interface for providing to a select individual electronic access to a health care history of the at least one eligible intervention candidate and the result of the comparison, the graphical user interface including a display of historical information based at least in part on the participant data associated with the at least one eligible intervention candidate and adapted to facilitate intervention in the health care regimen of the at least one eligible intervention candidate based on the result of the comparison, wherein the action score is determined based on a plurality of values, each value representing the intervention candidate's consumption of at least one of the plurality of different predetermined health care services.

12. The method of claim 11, wherein one of the plurality of values is selected from the group consisting of: a value representing a number of medical specialists that treated the candidate, a value representing a number of inpatient admissions, a value representing a number of chronic diseases for which the candidate was treated, a value representing a number of prescriptions for unique drugs, a value representing an amount of medical claims allowed, and a value representing a number of emergency room visits without admission in a hospital.

13. The method of claim 11 wherein at least one of the plurality of different predetermined health care services is selected from the group consisting of:
- a unique drug prescription;
- an instance of an inpatient admission;
- an existence of a chronic disease or condition;
- a unique medical specialty consultation;
- an allowed medical claim exceeding a predetermined monetary threshold; and
- an emergency room visit.

14. The method of claim 11 wherein the action score is determined based on a weighted matrix of values, each value associated with a corresponding scaling factor and representing the intervention candidate's consumption of at least one of the plurality of different predetermined health care services.

15. The method of claim 14 wherein one of the plurality of values in the matrix is selected from the group consisting of: a value representing a number of medical specialists that treated the candidate, a value representing a number of inpatient admissions, a value representing a number of chronic diseases for which the candidate was treated, a value representing a number of prescriptions for unique drugs, a value representing an amount of medical claims allowed, and a value representing a number of emergency room visits without admission in a hospital.

16. The method of claim 11 further comprising:
- executing a predictive model program using the participant data to generate an output, the predictive model program comprising logic to determine a likelihood of occurrence of at least one predetermined future event, the event associated with utilization of health care services, the logic having been created using historical claims data from a sample of individuals, the predictive model program being stored on the information server;
- determining, from the output of the execution of the predictive model program, via the information server, a predicted utilization score for an intervention candidate using the participant data, which score reflects a predicted utilization of future health care services; and
- evaluating the predicted utilization score to assist in identifying the at least one eligible intervention candidate.

17. The method of claim 11 wherein the information server is configured for generating a plurality of flags, wherein each flag has a status that represents the participant data associated with the intervention candidate.

18. The method of claim 17, wherein one of the plurality of flags represents the likelihood that an intervention candidate will claim disability under a disability insurance plan.

* * * * *